United States Patent
Aghdasi, Jr. et al.

(10) Patent No.: US 12,357,397 B2
(45) Date of Patent: Jul. 15, 2025

(54) METHODS AND SYSTEMS FOR CALIBRATING INSTRUMENTS WITHIN AN IMAGING SYSTEM, SUCH AS A SURGICAL IMAGING SYSTEM

(71) Applicant: Proprio, Inc., Seattle, WA (US)

(72) Inventors: Nava Aghdasi, Jr., Kirkland, WA (US); James Andrew Youngquist, Seattle, WA (US)

(73) Assignee: Proprio, Inc., Seattle, WA (US)

( * ) Notice: Subject to any disclaimer, the term of this patent is extended or adjusted under 35 U.S.C. 154(b) by 90 days.

(21) Appl. No.: 18/314,733

(22) Filed: May 9, 2023

(65) Prior Publication Data
US 2023/0355319 A1    Nov. 9, 2023

Related U.S. Application Data

(60) Provisional application No. 63/339,792, filed on May 9, 2022.

(51) Int. Cl.
*A61B 34/20*  (2016.01)
*A61B 90/00*  (2016.01)

(52) U.S. Cl.
CPC .............. *A61B 34/20* (2016.02); *A61B 90/39* (2016.02); *A61B 2034/2065* (2016.02); *A61B 2090/3937* (2016.02); *A61B 2560/0233* (2013.01)

(58) Field of Classification Search
CPC . A61B 34/20; A61B 90/39; A61B 2090/3937; A61B 2034/2055; A61B 2034/2057; A61B 2090/3983
See application file for complete search history.

(56) References Cited

U.S. PATENT DOCUMENTS 3,965,572 A    6/1976  Strybel
5,921,992 A *  7/1999  Costales ................ A61B 34/20
                                                            601/1

(Continued)

FOREIGN PATENT DOCUMENTS

EP    1570791 A1    9/2005
EP    1504713 B1    7/2008

(Continued)

OTHER PUBLICATIONS

International Search Report and Written Opinion received in Application No. PCT/US22/13490, dated May 6, 2022, 9 pages.

(Continued)

*Primary Examiner* — Oommen Jacob
(74) *Attorney, Agent, or Firm* — Perkins Coie LLP

(57) ABSTRACT

Methods and systems for calibrating an instrument, such as a surgical instrument, within an imaging system are disclosed herein. In some embodiments, a method includes capturing images of the instrument with a plurality of cameras of the imaging system and identifying common features of the instrument in the captured images. The method further includes generating a three-dimensional (3D) representation of the instrument based on the common features and determining a reference frame of the instrument based on the generated 3D representation of the instrument. A first transform is determined between the reference frame of the instrument and a reference frame of the cameras. Then, a second transform between the reference frame of the instrument and a reference frame of the tracking structure can be determined based on the first transform.

20 Claims, 9 Drawing Sheets

(56) References Cited

U.S. PATENT DOCUMENTS

| | | | |
|---|---|---|---|
| 5,987,960 A * | 11/1999 | Messner | A61B 17/00 73/1.79 |
| 6,167,295 A * | 12/2000 | Cosman | A61B 90/10 606/130 |
| 6,190,395 B1 | 2/2001 | Williams | |
| 6,351,659 B1 | 2/2002 | Vilsmeier | |
| 6,675,040 B1 | 1/2004 | Cosman | |
| 6,985,765 B2 | 1/2006 | Morita et al. | |
| 7,043,961 B2 * | 5/2006 | Pandey | A61B 34/20 73/1.79 |
| 7,153,297 B2 | 12/2006 | Peterson | |
| 7,226,456 B2 | 6/2007 | O'Neil et al. | |
| 7,519,415 B2 * | 4/2009 | Mitschke | A61B 34/20 702/150 |
| 8,165,839 B2 * | 4/2012 | Boese | A61B 5/062 73/1.79 |
| 8,182,469 B2 | 5/2012 | Anderson et al. | |
| 8,295,909 B2 | 10/2012 | Goldback | |
| 8,384,912 B2 | 2/2013 | Charny et al. | |
| 8,657,809 B2 | 2/2014 | Schoepp | |
| 8,800,939 B2 | 8/2014 | Karsak et al. | |
| 8,885,177 B2 | 11/2014 | Ben-Yishai | |
| D720,851 S | 1/2015 | Yang et al. | |
| 8,933,935 B2 | 1/2015 | Yang et al. | |
| 8,961,500 B2 | 2/2015 | DiCorleto et al. | |
| D727,497 S | 4/2015 | Yang et al. | |
| D768,296 S | 10/2016 | Corrao et al. | |
| D778,441 S | 2/2017 | Corrao et al. | |
| RE46,409 E | 5/2017 | Foley et al. | |
| 9,916,691 B2 | 3/2018 | Takano et al. | |
| 10,013,777 B2 | 7/2018 | Mariampillai et al. | |
| 10,034,713 B2 | 7/2018 | Yang et al. | |
| 10,074,177 B2 | 9/2018 | Piron et al. | |
| 10,143,523 B2 | 12/2018 | Mariampillai et al. | |
| 10,165,981 B2 | 1/2019 | Schoepp | |
| 10,194,131 B2 | 1/2019 | Casas | |
| 10,201,364 B2 | 2/2019 | Leimbach et al. | |
| 10,335,247 B2 | 7/2019 | Lechner et al. | |
| 10,398,514 B2 | 9/2019 | Ryan et al. | |
| 10,426,554 B2 | 10/2019 | Siewerdsen et al. | |
| 10,433,916 B2 | 10/2019 | Schneider et al. | |
| 10,463,434 B2 | 11/2019 | Siegler et al. | |
| 10,575,906 B2 | 3/2020 | Wu | |
| 10,650,573 B2 | 5/2020 | Youngquist et al. | |
| 10,653,495 B2 | 5/2020 | Gregerson et al. | |
| 10,667,868 B2 | 6/2020 | Malackowski | |
| 10,722,223 B2 | 7/2020 | Wehrli et al. | |
| 10,731,687 B2 | 8/2020 | Ponzer et al. | |
| 10,779,893 B2 | 9/2020 | Elliott et al. | |
| 10,799,304 B2 | 10/2020 | Kapadia et al. | |
| 10,806,539 B1 | 10/2020 | Richter et al. | |
| 10,810,799 B2 | 10/2020 | Tepper et al. | |
| 10,828,114 B2 | 11/2020 | Abhari et al. | |
| 10,881,530 B2 | 1/2021 | Donaldson et al. | |
| 10,893,912 B2 | 1/2021 | Crawford et al. | |
| 10,949,986 B1 | 3/2021 | Colmenares et al. | |
| 11,117,197 B2 | 9/2021 | Lindenmann et al. | |
| 11,172,994 B1 | 11/2021 | Seltmann et al. | |
| 11,272,995 B2 | 3/2022 | Landey et al. | |
| 11,406,381 B2 | 8/2022 | Parihar | |
| 11,896,446 B2 * | 2/2024 | Crawford | A61B 90/98 |
| 2002/0044631 A1 * | 4/2002 | Graumann | A61B 34/20 378/162 |
| 2002/0164067 A1 * | 11/2002 | Askey | G06T 17/20 382/154 |
| 2003/0029464 A1 * | 2/2003 | Chen | A61B 90/36 600/429 |
| 2003/0093904 A1 | 5/2003 | Makkonen | |
| 2003/0210812 A1 | 11/2003 | Khamene et al. | |
| 2003/0225329 A1 | 12/2003 | Rossner et al. | |
| 2004/0169673 A1 | 9/2004 | Crampe et al. | |
| 2005/0015005 A1 * | 1/2005 | Kockro | A61B 34/20 600/117 |
| 2005/0070789 A1 | 3/2005 | Aferzon | |
| 2005/0085717 A1 * | 4/2005 | Shahidi | A61B 34/20 600/443 |
| 2005/0096536 A1 | 5/2005 | Peterson et al. | |
| 2007/0008312 A1 * | 1/2007 | Zhou | G06T 7/80 345/419 |
| 2007/0239169 A1 | 10/2007 | Plaskos et al. | |
| 2008/0051768 A1 | 2/2008 | Stumpf | |
| 2009/0088634 A1 * | 4/2009 | Zhao | A61B 1/00193 600/425 |
| 2009/0306499 A1 | 12/2009 | Van et al. | |
| 2010/0099981 A1 | 4/2010 | Fishel | |
| 2011/0157373 A1 * | 6/2011 | Ye | G06T 7/85 348/187 |
| 2011/0263971 A1 | 10/2011 | Nikou et al. | |
| 2012/0078236 A1 * | 3/2012 | Schoepp | A61B 5/061 606/1 |
| 2012/0168587 A1 | 7/2012 | Karsak et al. | |
| 2013/0211421 A1 * | 8/2013 | Abovitz | A61B 90/90 606/130 |
| 2014/0288578 A1 | 9/2014 | Solar et al. | |
| 2015/0154806 A1 * | 6/2015 | Ogale | G06T 15/20 345/419 |
| 2015/0305701 A1 * | 10/2015 | Wendler | A61B 6/037 600/436 |
| 2016/0157938 A1 * | 6/2016 | Breisacher | G16H 30/20 382/128 |
| 2016/0191887 A1 * | 6/2016 | Casas | H04N 13/156 348/47 |
| 2016/0256225 A1 | 9/2016 | Crawford et al. | |
| 2016/0354582 A1 | 12/2016 | Yu et al. | |
| 2017/0000583 A1 | 1/2017 | Lechner et al. | |
| 2017/0116729 A1 * | 4/2017 | Stolka | A61B 5/067 |
| 2017/0202626 A1 | 7/2017 | Kula et al. | |
| 2018/0064496 A1 | 3/2018 | Hladio et al. | |
| 2018/0078316 A1 | 3/2018 | Schaewe et al. | |
| 2018/0140223 A1 * | 5/2018 | Kheradpir | A61B 34/20 |
| 2018/0150960 A1 * | 5/2018 | Derda | A61B 6/12 |
| 2019/0038362 A1 | 2/2019 | Nash et al. | |
| 2019/0129177 A1 | 5/2019 | Roimi et al. | |
| 2019/0183584 A1 | 6/2019 | Schneider et al. | |
| 2019/0209080 A1 | 7/2019 | Gullotti et al. | |
| 2019/0289284 A1 | 9/2019 | Smith et al. | |
| 2019/0290366 A1 | 9/2019 | Pettersson et al. | |
| 2019/0336222 A1 | 11/2019 | Schneider et al. | |
| 2020/0051280 A1 * | 2/2020 | Urban | G06T 7/50 |
| 2020/0105065 A1 | 4/2020 | Youngquist et al. | |
| 2020/0170718 A1 | 6/2020 | Peine | |
| 2020/0242755 A1 | 7/2020 | Schneider et al. | |
| 2020/0297427 A1 | 9/2020 | Cameron et al. | |
| 2021/0038340 A1 | 2/2021 | Itkowitz et al. | |
| 2021/0045618 A1 | 2/2021 | Stricko et al. | |
| 2021/0045813 A1 | 2/2021 | Wickham et al. | |
| 2021/0093394 A1 | 4/2021 | Yang et al. | |
| 2021/0106342 A1 | 4/2021 | Blackwell | |
| 2021/0113241 A1 | 4/2021 | Forster et al. | |
| 2021/0153953 A1 | 5/2021 | Mariampillai et al. | |
| 2021/0186527 A1 | 6/2021 | Biedermann et al. | |
| 2021/0192763 A1 | 6/2021 | Liu et al. | |
| 2021/0196385 A1 | 7/2021 | Shelton et al. | |
| 2021/0225020 A1 | 7/2021 | Nonn et al. | |
| 2021/0358139 A1 | 11/2021 | Colmenares et al. | |
| 2021/0390724 A1 | 12/2021 | Tilley et al. | |
| 2022/0071712 A1 | 3/2022 | Wolf et al. | |
| 2022/0125520 A1 | 4/2022 | Crawford et al. | |
| 2023/0355319 A1 * | 11/2023 | Aghdasi, Jr. | A61B 34/20 |

FOREIGN PATENT DOCUMENTS

| | | |
|---|---|---|
| EP | 2139419 A1 | 1/2010 |
| EP | 3197382 A1 | 8/2017 |
| EP | 1924197 B1 | 10/2017 |
| EP | 2774559 B1 | 12/2018 |
| EP | 3102141 B1 | 8/2019 |
| EP | 3076892 B1 | 10/2019 |
| EP | 3669812 A1 | 6/2020 |
| EP | 3046500 B1 | 8/2020 |
| WO | 2007115825 A1 | 10/2007 |
| WO | 2008130354 A1 | 10/2008 |

(56) References Cited

FOREIGN PATENT DOCUMENTS

| WO | 2010067267 A1 | 6/2010 |
| WO | 2017042171 A1 | 3/2017 |
| WO | 2020163316 A1 | 8/2020 |
| WO | 2021003401 A1 | 1/2021 |

OTHER PUBLICATIONS

International Search Report and Written Opinion received in Application No. PCT/US23/66792, dated Nov. 29, 2023, 30 pages.
U.S. Appl. No. 17/140,885, titled "Methods and Systems for Registering Preoperative Image Data To Intraoperative Image Data of a Scene, Such as a Surgical Scene," and filed Jan. 4, 2021.

\* cited by examiner

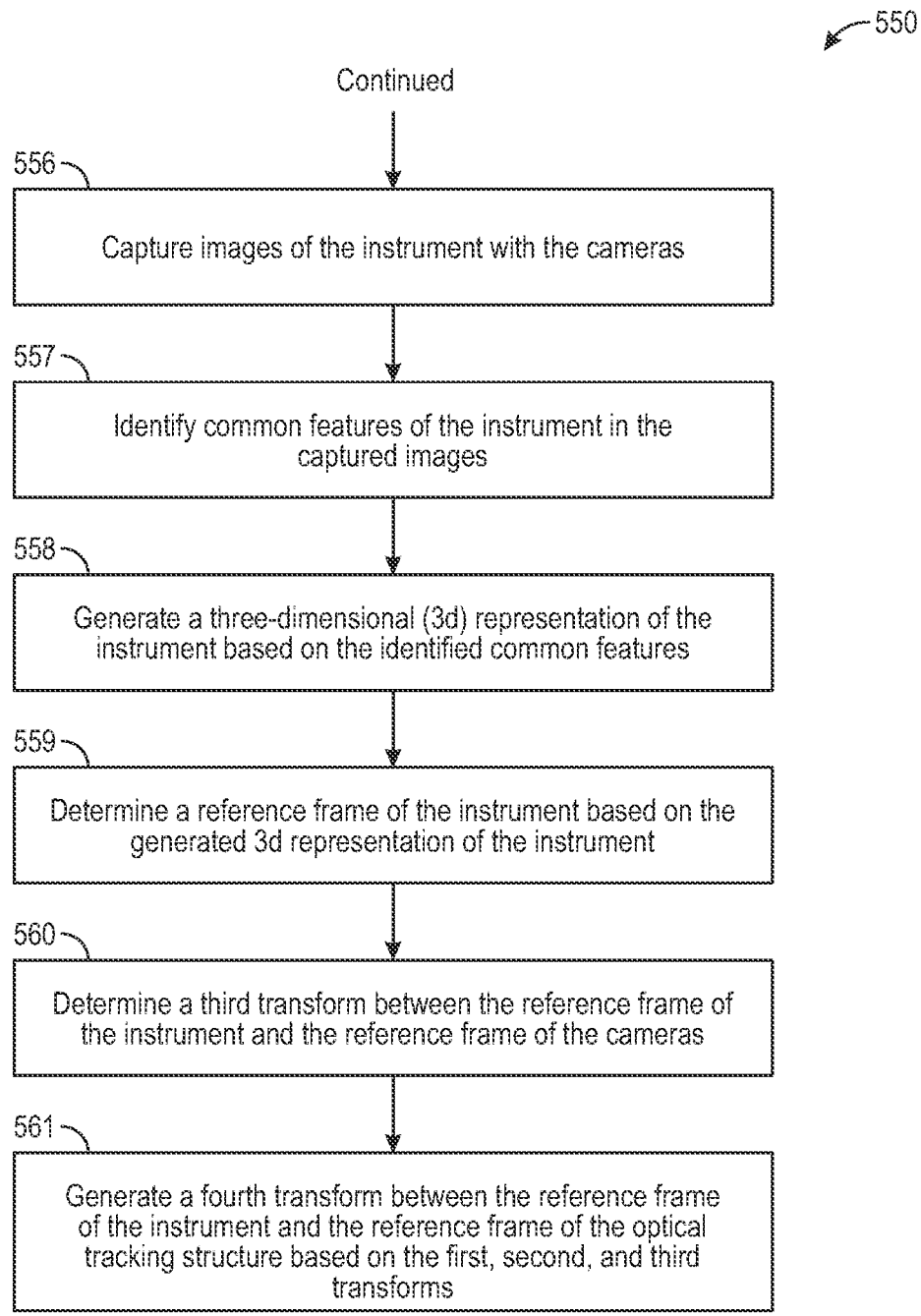
FIG. 5 (Contd.)

METHODS AND SYSTEMS FOR CALIBRATING INSTRUMENTS WITHIN AN IMAGING SYSTEM, SUCH AS A SURGICAL IMAGING SYSTEM

CROSS-REFERENCE TO RELATED APPLICATION

This application claims the benefit of U.S. Provisional Patent Application No. 63/339,792, filed May 9, 2022, and titled "METHODS AND SYSTEMS FOR CALIBRATING INSTRUMENTS WITHIN AN IMAGING SYSTEM, SUCH AS A SURGICAL IMAGING SYSTEM," which is incorporated herein by reference in its entirety.

TECHNICAL FIELD

The present technology generally relates to methods and systems for calibrating instruments within an imaging system, such as a surgical imaging system, for tracking.

BACKGROUND

Image-based navigation in surgery requires that surgical instruments be tracked and accurately calibrated for tracking. Optical tracking is the standard technique for surgical instrument navigation and is based on stereo or multi-view imaging of markers attached to a surgical instrument. The position and orientation of the markers in three-dimensional (3D) space are determined via triangulation. To translate the position and orientation of the markers to a 3D position and orientation of the surgical instrument, the spatial relationship between the markers and the instrument must be known (e.g., determined via calibration, during manufacturing). A 3D model can be used to represent the surgical instrument during image-based navigation. Any imprecision in the calibration of the markers to the instrument or in the tracking (e.g., triangulation) of the markers can lead to inaccuracies that are presented to the user. Discrepancies between the 3D model and the actual surgical instrument can also lead to inaccuracies.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1:
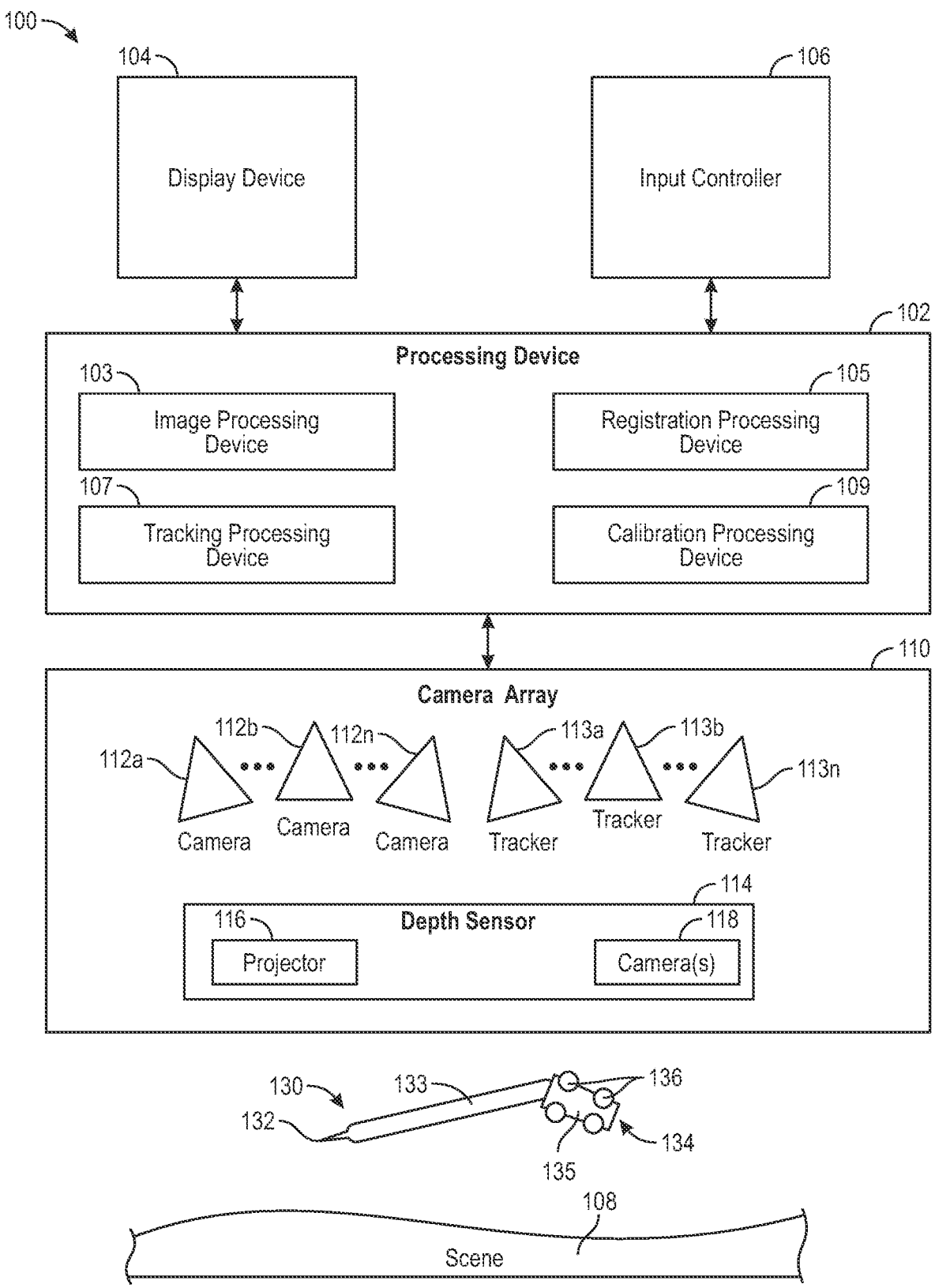
FIG. 1 is a schematic view of an imaging system in accordance with embodiments of the present technology.

Aspects of the present technology are directed generally to methods and systems for calibrating an instrument within an imaging system for tracking of the instrument. The instrument can be a surgical instrument (e.g., a spinal surgical instrument) to be tracked during a surgical procedure employing the surgical instrument (e.g., a spinal surgical procedure), or another type of instrument used in other imaging procedures. In several of the embodiments described below, the imaging system includes a camera array having (i) a plurality of cameras configured to image a scene including the instrument and (ii) a plurality of trackers for tracking a tracking structure (e.g., a constellation of marker balls) rigidly affixed to the instrument. The imaging system can be calibrated to determine a first transform between a reference frame of the cameras and a reference frame of the trackers, and a second transform between the reference frame of the trackers and a reference frame of the tracking structure.

In several of the embodiments described below, a representative method for calibrating the instrument within the imaging system includes capturing images of the instrument with the cameras and identifying common features of the instrument in the captured images. The images can be RGB images, hyperspectral images, or other types of images, and the common features can be points, lines, and the like indicating a tip, shaft, and/or physical feature of the instrument. The method can further include generating a three-dimensional (3D) representation of the instrument based on the common features, and determining a reference frame of the instrument based on the generated 3D representation of the instrument. The method can further include (i) determining a third transform between the reference frame of the instrument and the reference frame of the cameras and (ii) a fourth transform between the reference frame of the instrument and the reference frame of the tracking structure based on the first transform, the second transform, and the third transform. In some embodiments, the fourth transform can be calculated as the product of the first transform, the second transform, and the third transform. In some aspects of the present technology, the method can calibrate the instrument for tracking via the trackers without previous knowledge of the physical properties of the instrument and/or the spatial relationship between the optical tracking structure and the instrument.

Specific details of several embodiments of the present technology are described herein with reference to FIGS. 1-8. The present technology, however, can be practiced without some of these specific details. In some instances, well-known structures and techniques often associated with camera arrays, light field cameras, red-green-blue (RGB) cameras, hyperspectral cameras, camera calibration, registration processes, user interfaces, optical tracking, object tracking, marker balls, and the like have not been shown in detail so as not to obscure the present technology. Moreover, although frequently described in the context of surgical instruments within a surgical scene (e.g., a spinal surgical scene), the methods and systems of the present technology can be used to calibrate other instruments for tracking in other scenes.

The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. Depicted elements are not necessarily drawn to scale, and various elements can be arbitrarily enlarged to improve legibility. Component details can be abstracted in the figures to exclude details as such details are unnecessary for a complete understanding of how to make and use the present technology. Many of the details, dimensions, angles, and other features shown in the Figures are merely illustrative of particular embodiments of the disclosure. Accordingly, other embodiments can have other dimensions, angles, and features without departing from the spirit or scope of the present technology.

In the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1.

The headings provided herein are for convenience only and should not be construed as limiting the subject matter disclosed. To the extent any materials incorporated herein by reference conflict with the present disclosure, the present disclosure controls.

I. SELECTED EMBODIMENTS OF IMAGING SYSTEMS

FIG. 1 is a schematic view of an imaging system 100 ("system 100") in accordance with embodiments of the present technology. In some embodiments, the system 100 can be a synthetic augmented reality system, a virtual-reality imaging system, an augmented-reality imaging system, a mediated-reality imaging system, and/or a non-immersive computational imaging system. In the illustrated embodiment, the system 100 includes a processing device 102 that is communicatively coupled to one or more display devices 104, one or more input controllers 106, and a camera array 110. In other embodiments, the system 100 can comprise additional, fewer, or different components. In some embodiments, the system 100 includes some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," and filed May 12, 2020, each of which is incorporated herein by reference in its entirety.

In the illustrated embodiment, the camera array 110 includes a plurality of cameras 112 (identified individually as cameras 112a-112n; which can also be referred to as first cameras) that can each capture images of a scene 108 (e.g., first image data) from a different perspective. The scene 108 can include for example, a patient undergoing surgery (e.g., spinal surgery) and/or another medical procedure. In other embodiments, the scene 108 can be another type of scene. The camera array 110 can further include dedicated object tracking hardware 113 (e.g., including individually identified trackers 113a-113n) that captures positional data of one or more objects—such as an instrument 130 (e.g., a surgical instrument or tool) having a tip 132 and a shaft 133—to track the movement and/or orientation of the objects through/in the scene 108. In some embodiments, the cameras 112 and the trackers 113 are positioned at fixed locations and orientations (e.g., poses) relative to one another. For example, the cameras 112 and the trackers 113 can be structurally secured by/to a mounting structure (e.g., a frame) at predefined fixed locations and orientations. In some embodiments, the cameras 112 are positioned such that neighboring cameras 112 share overlapping views of the scene 108. In general, the position of the cameras 112 can be selected to maximize clear and accurate capture of all or a selected portion of the scene 108. Likewise, the trackers 113 can be positioned such that neighboring trackers 113 share overlapping views of the scene 108. Therefore, all or a subset of the cameras 112 and the trackers 113 can have different extrinsic parameters, such as position and orientation.

In some embodiments, the cameras 112 in the camera array 110 are synchronized to capture images of the scene 108 simultaneously (within a threshold temporal error). In some embodiments, all or a subset of the cameras 112 are light field/plenoptic/RGB cameras that capture information about the light field emanating from the scene 108 (e.g., information about the intensity of light rays in the scene 108 and also information about a direction the light rays are traveling through space). Therefore, in some embodiments the images captured by the cameras 112 encode depth information representing a surface geometry of the scene 108. In some embodiments, the cameras 112 are substantially identical. In other embodiments, the cameras 112 include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses. For example, the cameras 112 can be separate light field cameras each having their own image sensors and optics. In other embodiments, some or all of the cameras 112 can comprise separate microlenslets (e.g., lenslets, lenses, microlenses) of a microlens array (MLA) that share a common image sensor.

In some embodiments, the trackers 113 are imaging devices, such as infrared (IR) cameras that can capture images of the scene 108 from a different perspective compared to other ones of the trackers 113. Accordingly, the trackers 113 and the cameras 112 can have different spectral sensitives (e.g., infrared vs. visible wavelength). In some embodiments, the trackers 113 capture image data of a plurality of optical markers (e.g., fiducial markers, retroreflective markers, marker balls) in the scene 108. For example, in the illustrated embodiment an optical tracking structure 134 is coupled to the instrument 130. The optical tracking structure 134 can include a constellation or support 135 rigidly attached to shaft 133 of the instrument 130 and a plurality of markers 136 rigidly attached to the support 135 such that the markers 136 are fixed in position relative to the tip 132 and the shaft 133. The markers 136 can be visible to the trackers 113 and/or an auxiliary tracking unit (e.g., positioned external to the camera array 110).

In the illustrated embodiment, the camera array 110 further includes a depth sensor 114. In some embodiments, the depth sensor 114 includes (i) one or more projectors 116 that project a structured light pattern onto/into the scene 108 and (ii) one or more depth cameras 118 (which can also be referred to as second cameras) that capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the camera array 110 can omit the projector 116 and/or the depth cameras 118.

In the illustrated embodiment, the processing device 102 includes an image processing device 103 (e.g., an image processor, an image processing module, an image processing unit), a registration processing device 105 (e.g., a registration processor, a registration processing module, a registration processing unit), a tracking processing device 107 (e.g., a tracking processor, a tracking processing module, a tracking processing unit), and a calibration processing device 109 (e.g., a calibration processor, a calibration processing module, a calibration processing unit). The image processing device 103 can (i) receive the first image data captured by the cameras 112 (e.g., light field images, light field image data, RGB images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 103 can further receive and/or store calibration data for the cameras 112 and/or the depth cameras 118 and synthesize the output image based on the image data, the depth information, and/or the calibration data. More specifically, the depth information and the calibration data can be used/combined with the images from the cameras 112 to synthesize the output image as a 3D (or stereoscopic 2D) rendering of the scene 108 as viewed from the virtual camera perspective. In some embodiments, the image processing device 103 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," and filed Jun. 28, 2019, which is incorporated herein by reference in its entirety. In other embodiments, the image processing device 103 can generate the virtual camera perspective based only on the images captured by the cameras 112—without utilizing depth information from the depth sensor 114. For example, the image processing device 103 can generate the virtual camera perspective by interpolating between the different images captured by one or more of the cameras 112.

The image processing device 103 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112. In some embodiments, such a stereoscopic pair can be selected to be positioned and oriented to most closely match the virtual camera perspective. In some embodiments, the image processing device 103 (and/or the depth sensor 114) estimates a depth for each surface point of the scene 108 relative to a common origin to generate a point cloud and/or a 3D mesh that represents the surface geometry of the scene 108. Such a representation of the surface geometry can be referred to as a depth map, an N35 surface, a depth surface, and/or the like. In some embodiments, the depth cameras 118 of the depth sensor 114 detect the structured light projected onto the scene 108 by the projector 116 to estimate depth information of the scene 108. In some embodiments, the image processing device 103 estimates depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, the registration processing device 105 receives and/or stores previously-captured image data, such as image data of a three-dimensional volume of a patient (3D image data). The image data can include, for example, computerized tomography (CT) scan data, magnetic resonance imaging (MRI) scan data, ultrasound images, fluoroscope images, and/or other medical or other image data. The registration processing device 105 can register the preoperative image data to the real-time images captured by the cameras 112 and/or the depth sensor 114 by, for example, determining one or more transforms/transformations/mappings between the two. The processing device 102 (e.g., the image processing device 103) can then apply the one or more transforms to the preoperative image data such that the preoperative image data can be aligned with (e.g., overlaid on) the output image of the scene 108 in real-time or near real time on a frame-by-frame basis, even as the virtual perspective changes. That is, the image processing device 103 can fuse the preoperative image data with the real-time output image of the scene 108 to present a mediated-reality view that enables, for example, a surgeon to simultaneously view a surgical site in the scene 108 and the underlying 3D anatomy of a patient undergoing an operation. In some embodiments, the registration processing device 105 can register the previously-captured image data to the real-time images using any of the methods disclosed in U.S. patent application Ser. No. 17/140,885, titled "METHODS AND SYSTEMS FOR REGISTERING PREOPERATIVE IMAGE DATA TO INTRAOPERATIVE IMAGE DATA OF A SCENE, SUCH AS A SURGICAL SCENE," and filed Jan. 4, 2021.

In some embodiments, the tracking processing device 107 processes positional data captured by the trackers 113 to track objects (e.g., the instrument 130) within the vicinity of the scene 108. For example, the tracking processing device 107 can determine the position of the markers 136 in the 2D images captured by two or more of the trackers 113, and can compute the 3D position of the markers 136 via triangulation of the 2D positional data. More specifically, in some embodiments the trackers 113 include dedicated processing hardware for determining positional data from captured images, such as a centroid of the markers 136 in the captured images. The trackers 113 can then transmit the positional data to the tracking processing device 107 for determining the 3D position of the markers 136. In other embodiments, the tracking processing device 107 can receive the raw image data from the trackers 113. In a surgical application, for example, the tracked object can comprise a surgical instrument, an implant, a hand or arm of a physician or assistant, and/or another object having the markers 136 mounted thereto. In some embodiments, the processing device 102 can recognize the tracked object as being separate from the scene 108, and can apply a visual effect to the 3D output image to distinguish the tracked object by, for example, reproducing a 3D visualization (e.g., model) of the object, highlighting the object, labeling the object, and/or applying a transparency to the object.

In some embodiments, the calibration processing device 109 calibrates the instrument 130 within the system 100 for tracking and/or verifies the calibration of the instrument 130 as described in detail below with reference to FIGS. 4-8. For example, the calibration processing device 109 can (i) generate a 3D representation of the instrument 130 based on image data received from the cameras 112 and (ii) determine a calibration transform between the 3D representation of the instrument 130 and the optical tracking structure 134. Based on the calibration transform, the calibration processing device 109 can accurately represent/display the 3D visualization of the instrument 130 within the output image of the scene 108 based on the real-time or near real-time tracked position of the markers 136 determined/captured by the trackers 113.

In some embodiments, functions attributed to the processing device 102, the image processing device 103, the registration processing device 105, the tracking processing device 107, and/or the calibration processing device 109 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multicamera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective is controlled by an input controller 106 that can update the virtual camera perspective based on user driven changes to the camera's position and rotation. The output images corresponding to the virtual camera perspective can be outputted to the display device 104. In some embodiments, the image processing device 103 can vary the perspective, the depth of field (e.g., aperture), the focus plane, and/or another parameter of the virtual camera (e.g., based on an input from the input controller) to generate different 3D output images without physically moving the camera array 110. The display device 104 can receive output images (e.g., the synthesized 3D rendering of the scene 108) and display the output images for viewing by one or more viewers. In some embodiments, the processing device 102 receives and processes inputs from the input controller 106 and processes the captured images from the camera array 110 to generate output images corresponding to the virtual perspective in substantially real-time or near real-time as perceived by a viewer of the display device 104 (e.g., at least as fast as the frame rate of the camera array 110).

Additionally, the display device 104 can display a graphical representation on/in the image of the virtual perspective of any (i) tracked objects within the scene 108 (e.g., the instrument 130) and/or (ii) registered or unregistered preoperative image data. That is, for example, the system 100 (e.g., via the display device 104) can blend augmented data into the scene 108 by overlaying and aligning information on top of "passthrough" images of the scene 108 captured by the cameras 112. Moreover, the system 100 can create a mediated-reality experience where the scene 108 is reconstructed using light field image date of the scene 108 captured by the cameras 112, and where instruments are virtually represented in the reconstructed scene via information from the trackers 113. Additionally or alternatively, the system 100 can remove the original scene 108 and completely replace it with a registered and representative arrangement of the preoperatively captured image data, thereby removing information in the scene 108 that is not pertinent to a user's task.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. In some embodiments, the system 100 can further include a separate tracking system (not shown), such an optical tracking system, for tracking the display device 104, the instrument 130, and/or other components within the scene 108. Such a tracking system can detect a position of the head-mounted display device 104 and input the position to the input controller 106. The virtual camera perspective can then be derived to correspond to the position and orientation of the head-mounted display device 104 in the same reference frame and at the calculated depth (e.g., as calculated by the depth sensor 114) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller) that enables a viewer to manually control the virtual perspective displayed by the display device 104.

Figure 2:
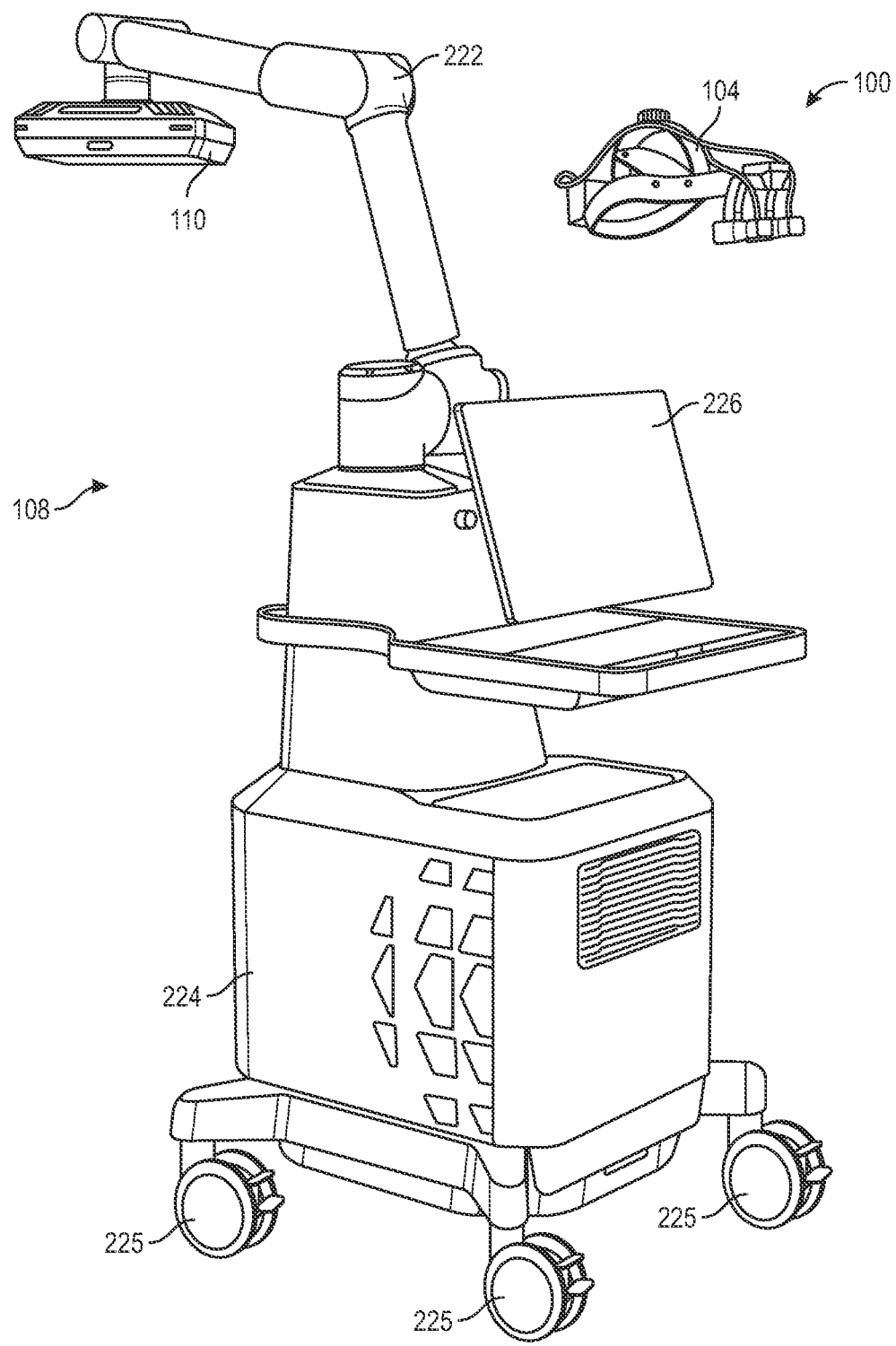
FIG. 2 is a perspective view of a surgical environment employing the imaging system of FIG. 1 for a surgical application in accordance with embodiments of the present technology.

FIG. 2 is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 is manually movable to position the camera array 110 while, in other embodiments, the arm 222 is robotically controlled in response to the input controller 106 (FIG. 1) and/or another controller. In the illustrated embodiment, the workstation 224 is mounted on wheels or casters 225 that allow the system 100 to be rolled. In some embodiments, the system 100 can be rolled on the casters 225 and/or the arm 222 can be moved to scan a region of the scene 108, such as a portion of a patient's spine.

In the illustrated embodiment, the display device 104 is a head-mounted display device (e.g., a virtual reality headset, augmented reality headset). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications. In other embodiments, the system 100 can include more or fewer display devices. For example, in addition to the display device 104 and the secondary display 226, the system 100 can include another display (e.g., a medical grade computer monitor) visible to the user wearing the display device 104.

Figure 3:
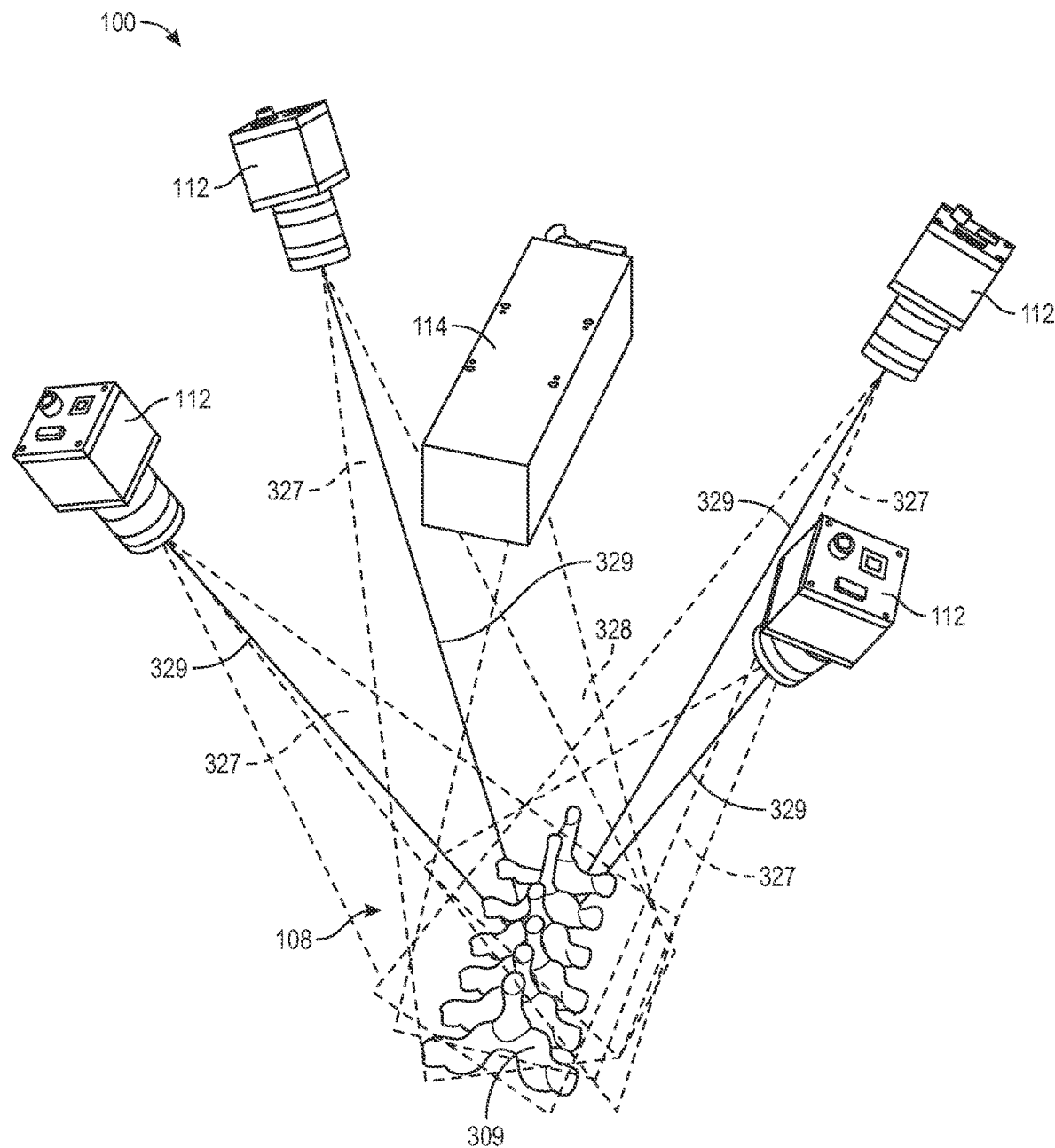
FIG. 3 is an isometric view of a portion of the imaging system of FIG. 1 illustrating four cameras of the imaging system in accordance with embodiments of the present technology.

FIG. 3 is an isometric view of a portion of the system 100 illustrating four of the cameras 112 in accordance with embodiments of the present technology. Other components of the system 100 (e.g., other portions of the camera array 110, the processing device 102, etc.) are not shown in FIG. 3 for the sake of clarity. In the illustrated embodiment, each of the cameras 112 has a field of view 327 and a focal axis 329. Likewise, the depth sensor 114 can have a field of view 328 aligned with a portion of the scene 108. The cameras 112 can be oriented such that the fields of view 327 are aligned with a portion of the scene 108 and at least partially overlap one another to together define an imaging volume. In some embodiments, some or all of the field of views 327, 328 at least partially overlap. For example, in the illustrated embodiment the fields of view 327, 328 converge toward a common measurement volume including a portion of a spine 309 of a patient (e.g., a human patient) located in/at the scene 108. In some embodiments, the cameras 112 are further oriented such that the focal axes 329 converge to a common point in the scene 108. In some aspects of the present technology, the convergence/alignment of the focal axes 329 can generally maximize disparity measurements between the cameras 112. In some embodiments, the cameras 112 and the depth sensor 114 are fixedly positioned relative to one another (e.g., rigidly mounted to a common frame) such that the positions of the cameras 112 and the depth sensor 114 relative to one another is known and/or can be readily determined via a calibration process. In other embodiments, the system 100 can include a different number of the cameras 112 and/or the cameras 112 can be positioned differently relative to another. In some embodiments, the camera array 110 can be moved (e.g., via the arm 222 of FIG. 2) to move the fields of view 327, 328 to, for example, scan the spine 309.

Referring to FIGS. 1-3 together, in some aspects of the present technology the system 100 can generate a digitized view of the scene 108 that provides a user (e.g., a surgeon) with increased "volumetric intelligence" of the scene 108. For example, the digitized scene 108 can be presented to the user from the perspective, orientation, and/or viewpoint of their eyes such that they effectively view the scene 108 as though they were not viewing the digitized image (e.g., as though they were not wearing the head-mounted display 104). However, the digitized scene 108 permits the user to digitally rotate, zoom, crop, or otherwise enhance their view to, for example, facilitate a surgical workflow. Likewise, preoperative image data, such as CT scans, can be registered to and overlaid over the image of the scene 108 to allow a surgeon to view these data sets together. Such a fused view can allow the surgeon to visualize aspects of a surgical site that may be obscured in the physical scene 108—such as regions of bone and/or tissue that have not been surgically exposed.

II. SELECTED EMBODIMENTS OF METHODS AND SYSTEMS FOR CALIBRATING INSTRUMENTS WITHIN AN IMAGING SYSTEM

Referring to FIG. 1, to accurately track the instrument 130 within the scene 108 via the trackers 113 and represent the instrument 130 in image data captured by the cameras 112, the system 100 must be calibrated/co-calibrated. The calibration determines the spatial and positional relationships between the different reference frames (e.g., coordinate frames) of the cameras 112, the trackers 113, the instrument 130, and the optical tracking structure 134 such that data captured in one reference frame can be translated/transformed to another reference frame.

Figure 4:
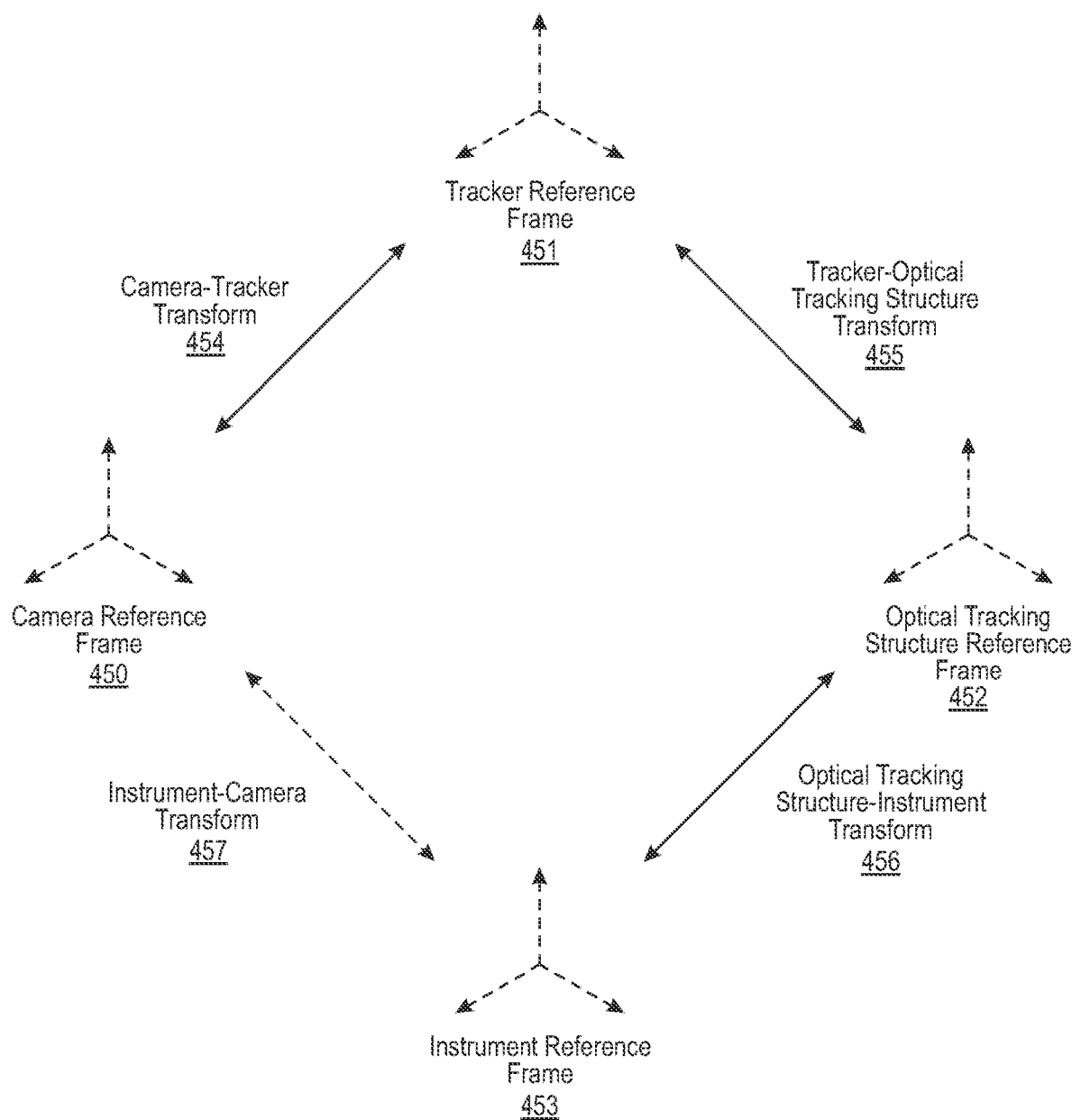
FIG. 4 is a schematic diagram of a calibration of the imaging system of FIG. 1 in accordance with embodiments of the present technology.

More specifically, for example, FIG. 4 is a schematic diagram of a calibration of the system 100 in accordance with embodiments of the present technology. Referring to FIGS. 1 and 4 together, (i) the cameras 112 define a camera reference frame 450, (ii) the trackers 113 define a tracker reference frame 451, (iii) the optical tracking structure 134 defines an optical tracking structure reference frame 452, and (iv) the instrument 130 defines an instrument reference frame 453. The calibration process can determine (i) a camera-tracker (CT) transform 454 (e.g., a first transform) for computing/translating between the camera reference frame 450 and the tracker reference frame 451, (ii) a tracker-optical tracking structure (T-OTS) transform 455 (e.g., a second transform) for computing between the tracker reference frame 451 and the optical tracking structure reference frame 452, and (iii) an optical tracking structure-instrument (OTS-I) transform 456 (e.g., a third transform) for computing between the optical tracking structure reference frame 452 and the instrument reference frame 453. That is, the transforms 454-456 allow the system 100 to express measurements determined relative to any of the reference frames 450-453 in a common reference frame.

After calibration, when each of the parameters 450-456 is known, the system 100 can determine the position and orientation of the instrument 130 within the scene 108 (e.g., within the common reference frame) by tracking the markers 136. The system 100 can therefore present a visual representation of the instrument 130 in one or more output images of the scene 108 generated from images captured by the cameras 112.

In some embodiments, the system 100 receives a three-dimensional (3D) model of the instrument 130 to determine the instrument reference frame 453. When the instrument is rotationally symmetric, the 3D model can specify a principal axis of the instrument 130 and a location of the tip 132 of the instrument 130, among other physical parameters of the instrument 130. In some embodiments, when the instrument 130 is not symmetric, the 3D model can specify two or more axes of the instrument 130 among other physical parameters. Further, to determine the OTS-I transform 456, the system 100 can receive a known (e.g., fixed) spatial relationship between the instrument 130 and the optical tracking structure 134. For example, the spatial relationship can be specified during manufacture of the instrument 130. Sometimes, however, a 3D model of the instrument 130 and/or the spatial relationship between the instrument 130 and the optical tracking structure 134 is not known. That is, the instrument reference frame 453 and the OTS-I transform 456 can be unknown—such as when the instrument 130 is a novel instrument that is currently unknown to the system 100. In some such embodiments, the system 100 can calibrate the instrument 130 within the system 100 for tracking by calculating the instrument reference frame 453 and the OTS-I transform 456 based on images of the instrument 130 captured by the cameras 112.

Figure 5:
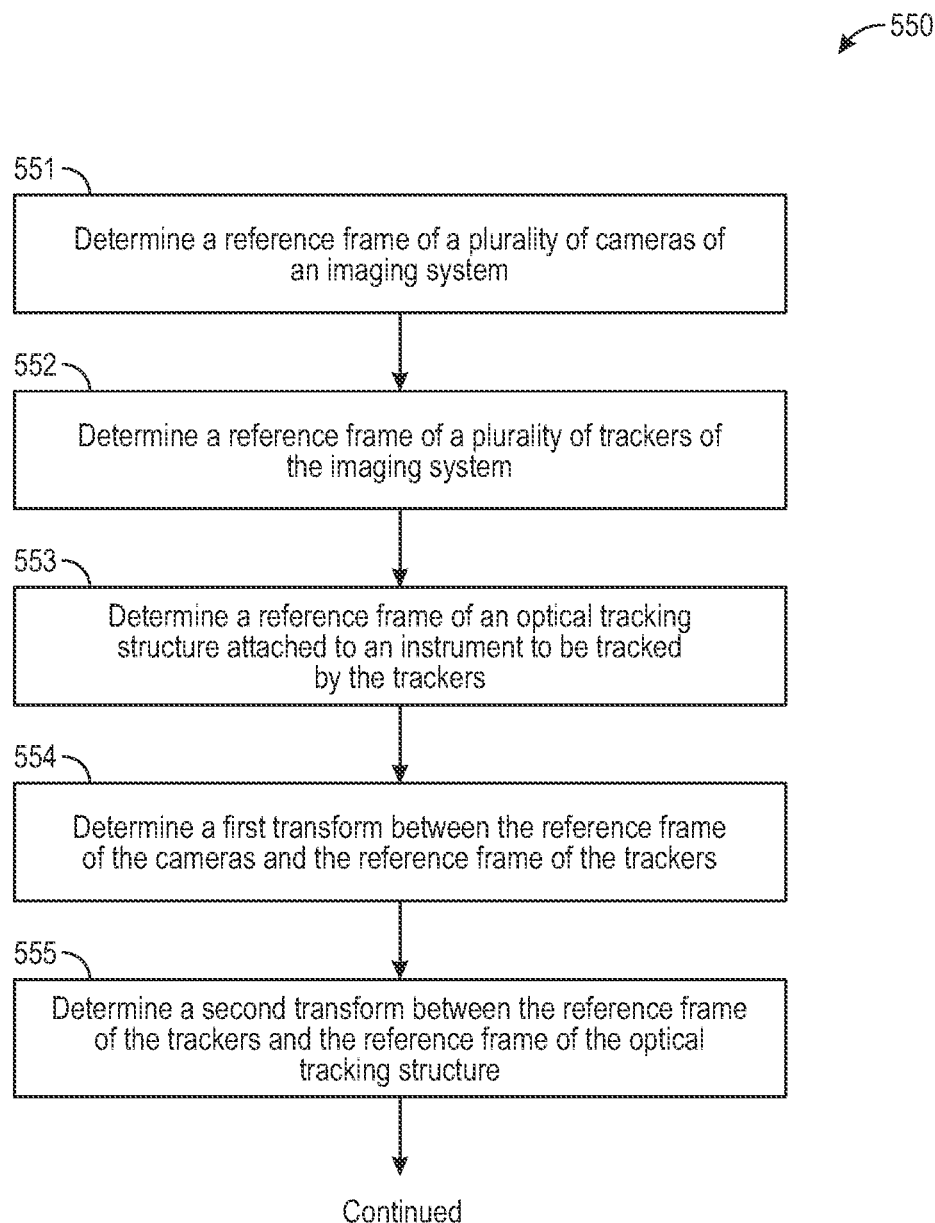
FIG. 5 is a flow diagram of a process or method for calibrating an instrument within the imaging system of FIG. 1 in accordance with embodiments of the present technology.

More specifically, FIG. 5 is a flow diagram of a process or method 550 for calibrating the instrument 130 within the imaging system 100 in accordance with embodiments of the present technology. The method 550 can be carried out even where the physical parameters of the instrument 130 and the spatial relationship between the optical tracking structure 134 and the instrument 130 are not known. Although some features of the method 550 are described in the context of the system 100 shown in FIGS. 1-4 for the sake of illustration, one skilled in the art will readily understand that the method 550 can be carried out using other suitable systems and/or devices described herein. Similarly, while reference is made herein to calibrating the instrument 130, the method 550 can be used to calibrate all or a portion of other objects within the scene 108 (e.g., an arm of a surgeon, additional instruments, etc.) including optical tracking markers affixed thereto. The scene 108 can be a surgical scene or other type of scene.

At block 551, the method 550 can include determining the camera reference frame 450 of the cameras 112. In some embodiments, determining the camera reference frame 450 includes calibrating (e.g., both intrinsically and extrinsically) the cameras 112 such that, after calibration, image data from each of the spaced apart cameras 112 can be represented in the same reference frame. In some embodiments, the calibration processing device 109 performs a calibration process to detect the positions and orientation of each of the cameras 112 in 3D space with respect to a shared origin and/or an amount of overlap in their respective fields of view. For example, the calibration processing device 109 can (i) process captured images from each of the cameras 112 including a fiducial marker placed in the scene 108 and (ii) perform an optimization over the camera parameters and distortion coefficients to minimize reprojection error for key points (e.g., points corresponding to the fiducial markers). In some embodiments, the calibration processing device 109 performs the calibration process by correlating feature points across different cameras views. The correlated features can be, for example, reflective marker centroids from binary images, scale-invariant feature transforms (SIFT) features from grayscale or color images, and the like. In some embodiments, the calibration processing device 109 extracts feature points from a target (e.g., a ChArUco target) imaged by the cameras 112 and processes the feature points with the OpenCV camera calibration routine. In other embodiments, such a calibration can be performed with a Halcon circle target or other custom target with well-defined feature points with known locations. In some embodiments, further calibration refinement can be carried out using bundle analysis and/or other suitable techniques.

At block 552, the method 550 can include determining the tracker reference frame 451 of the trackers 113. In some embodiments, determining the tracker reference frame 451 includes calibrating (e.g., both intrinsically and extrinsically) the trackers 113 such that, after calibration, tracking data from each of the spaced apart trackers 113 can be represented in the same reference frame. The calibration process for the trackers 113 can be generally similar or identical to that of the cameras 112 described in detail above with reference to block 552. For example, the calibration processing device 109 can extract feature points from a target imaged by the trackers 113 and process the feature points with the OpenCV camera calibration routine.

At block 553, the method 550 can include determining the optical tracking structure reference frame 452 of the optical tracking structure 134. In some embodiments, determining the optical tracking structure reference frame 452 includes receiving/determining a physical arrangement of the fixed markers 136 relative to one another such that, for example, the position and orientation of the optical tracking structure 134 is fully specified by the position and orientation of the markers 136.

At block 554, the method 550 can include determining a first transform (e.g., the C-T transform 454) between the camera reference frame 450 and the tracker reference frame 451. In some embodiments, determining the C-T transform 454 includes co-calibrating the cameras 112 and the trackers 113 based on imaging of a known target in the scene 108. Where the spectral sensitivity of the cameras 112 and the trackers 113 does not overlap, the target can be a multispectral target including, for example, a pattern that is visible to the cameras 112 and a plurality of optical markers (e.g., retroreflective markers) that are visible to the trackers 113 and that share a common origin and coordinate frame. In some embodiments, the C-T transform 454 is set after an initial calibration and does not need to be updated (e.g., during a surgical procedure using the system 100) because the cameras 112 and the trackers 113 are fixed relative to one another. In other embodiments, the C-T transform 454 can be updated (e.g., recalibrated) to account for, for example, positional and/or orientational shifts due to heat, thermal cycling, vibration, movement, and the like.

At block 555, the method 550 includes determining a second transform (e.g., the T-OTS transform 455) between the tracker reference frame 451 and the optical tracking structure reference frame 452. In some embodiments, the calibration processing device 109 and/or the tracking processing device 107 determines the T-OTS transform 455 by imaging the optical tracking structure 134 with the trackers 113 to calculate a pose (e.g., position and orientation) of the markers 136 relative to the trackers 113. Because the optical tracking structure 134 is not fixed in position and orientation relative to the trackers 113, the system 100 can update the T-OTS transform 455 in real-time or near real-time as the instrument 130 and the attached optical tracking structure 134 are moved through the scene 108 (e.g., during a surgical procedure) based on the real-time or near real-time tracking data captured by the trackers 113.

In some embodiments, one or more of blocks 551-555 can include features generally similar to or identical to those of U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," and filed May 12, 2020, which is incorporated herein by reference in its entirety. In some embodiments, some or all of blocks 551, 552, and 554 can be combined into a single calibration step based on imaging of a common target where, for example, the target is configured (e.g., shaped, sized, precisely manufactured) to allow for calibration points to be uniformly sampled over the desired tracking volume.

After block 555, the reference frames 450-452 and the transforms 454-455 are known, but the instrument reference frame 453 and the OTS-I transform 456 remain unknown. Blocks 556-560 illustrate several representative steps for determining the instrument reference frame 453 and the OTS-I transform 456 such that the system 100 can be fully calibrated for (i) tracking the instrument 130 through the scene 108 and (ii) matching the tracking data to image data captured by the cameras 112.

Figure 6:
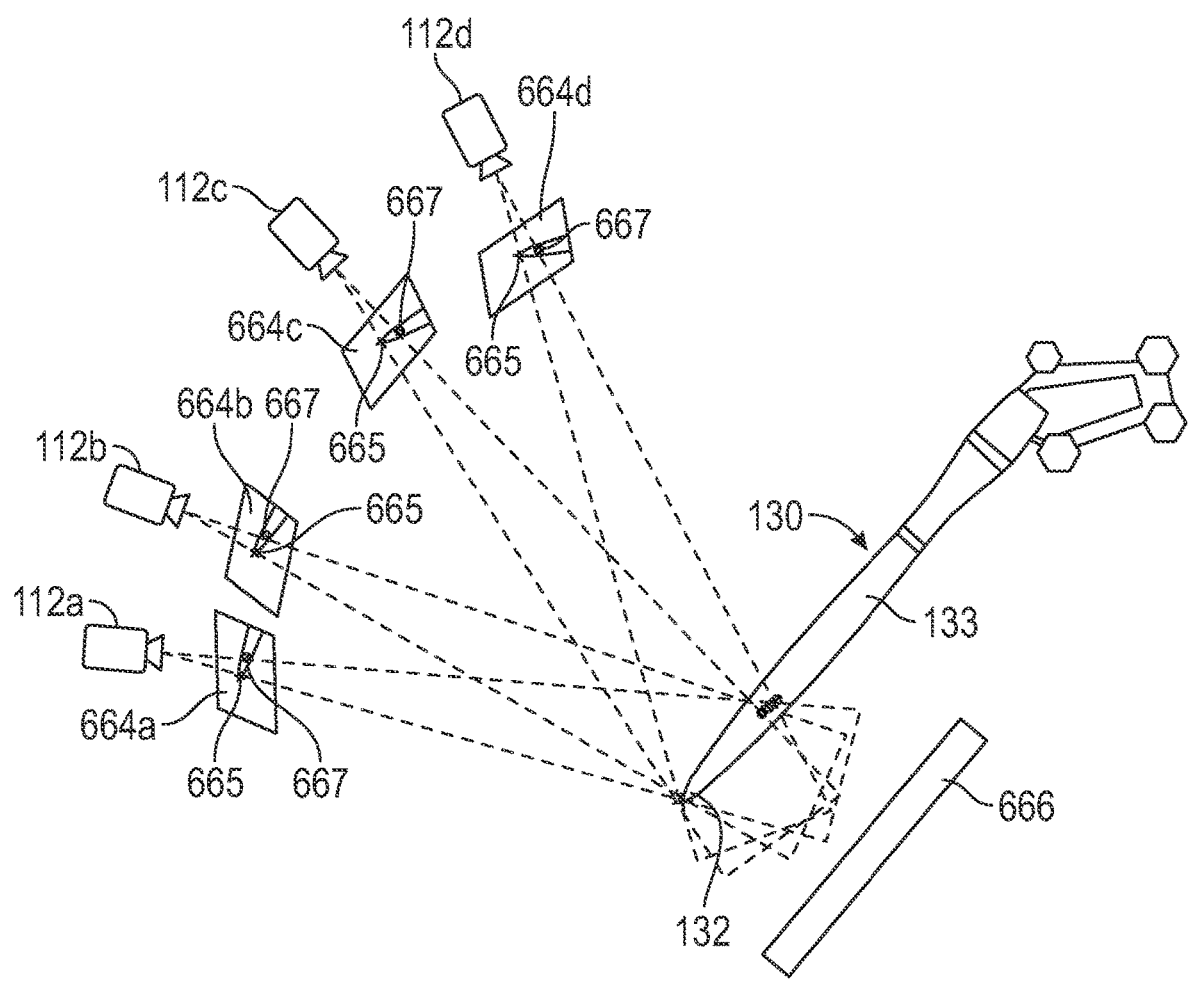
FIG. 6 is a schematic view of images of an instrument captured by cameras of the imaging system of FIG. 1 in accordance with embodiments of the present technology.

At block 556, the method 550 can include capturing images of the instrument 130 with the cameras 112. FIG. 6, for example, is a schematic view of first through fourth images 664*a-d* of the instrument 130, respectively, captured by first through fourth ones of the cameras 112*a-d*, respectively, in accordance with embodiments of the present technology. As shown, the cameras 112 are each positioned and/or oriented differently relative to one another such that each of the images 664 captures a different perspective of the instrument 130. FIGS. 7A-7D, for example, are further representative images 664 of the instrument 130 captured by the cameras 112 in accordance with embodiments of the present technology. In the illustrated embodiment, the images 664 each include image data of the tip 132 and at least a portion of the shaft 133 of the instrument 130. In some embodiments, the images 664 are RGB images.

Figure 8:
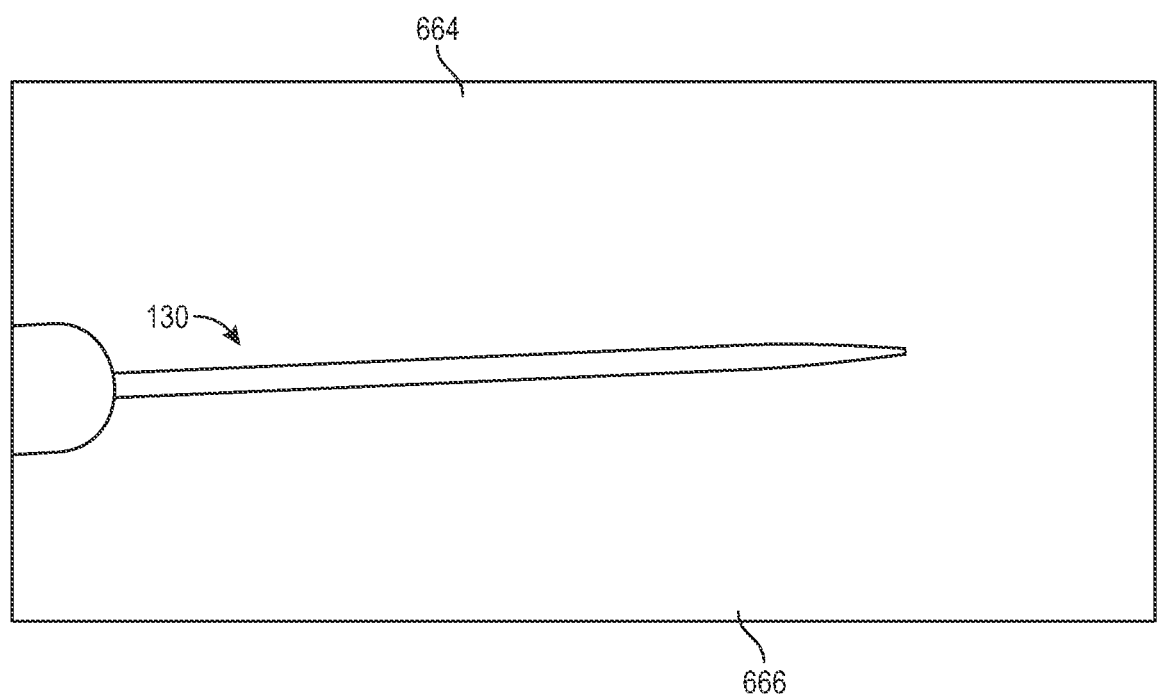
FIG. 8 is an image an instrument captured by a camera of the imaging system of FIG. 1 against a controlled background in accordance with embodiments of the technology.

Referring to FIG. 6, in some embodiments the instrument 130 is positioned against a controlled background 666 during imaging. The background 666 can be a chromakey (e.g., a "green screen") or backlight and, in some embodiments, can be displayed on the secondary monitor 226 (FIG. 2) and/or another display of the system 100. FIG. 8, for example, is another representative image 664 of the instrument 130 captured by one of the cameras 112 against the background 666 when the background 666 includes a chromakey in accordance with embodiments of the technology. In a backlit arrangement, the background 666 can comprise a light-emitting source (e.g., a uniform light-emitting source) and the instrument 130 can be positioned between the light-emitting source and the cameras 112 such that the images captured with the cameras 112 are substantially binary images. Such binary images can be high resolution, accurate, and easily segmental. In some embodiments, the background 666 comprises all or a portion of a light diffuser such that images captured with the cameras 112 are substantially binary images. The diffuser can also incorporate a known mechanical feature (e.g., a cross or "X") for locating the instrument 130 (e.g., for placing the tip 132 of the instrument 130) to further ease detection and increase accuracy of further processing steps (e.g., subsequent blocks 557-558).

Referring again to FIG. 6, in some embodiments the cameras 112 can each capture multiple images of the instrument 130 such that the total number of images 664 is greater than four. For example, the camera array 110 can be moved about the scene 108 to capture multiple images 664 of the instrument 130 from different perspectives and/or the instrument 130 can be moved relative to the cameras 112 and multiple images 664 taken when the instrument 130 is positioned differently relative to the cameras 112. In some aspects of the present technology, increasing the number of images 664 captured can reduce an error level in subsequent processing steps (e.g., blocks 557-561).

Figure 7A:
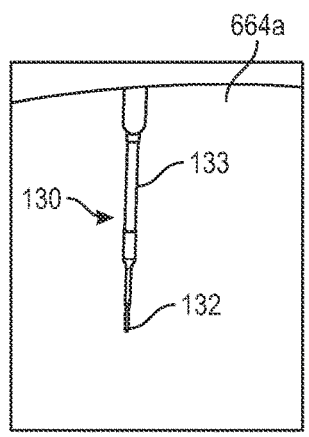
FIGS. 7A-7D are images of an instrument captured by cameras of the imaging system of FIG. 1 in accordance with embodiments of the present technology.
Figure 7B:
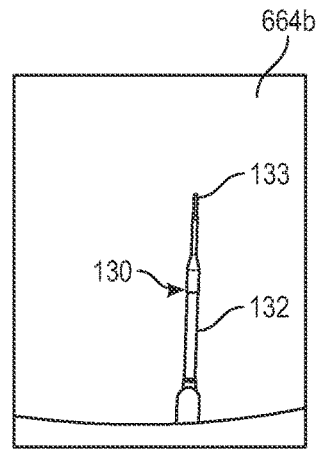
Figure 7C:
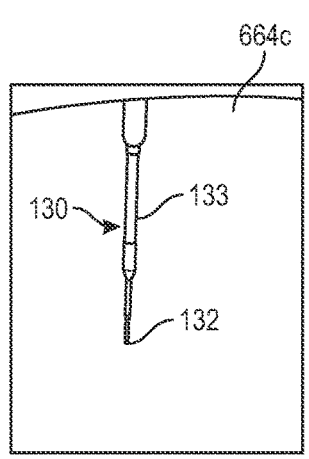
Figure 7D:
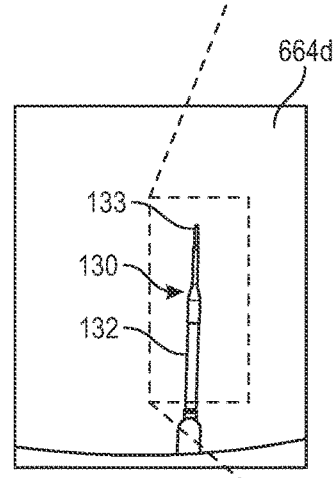
Figure 7E:
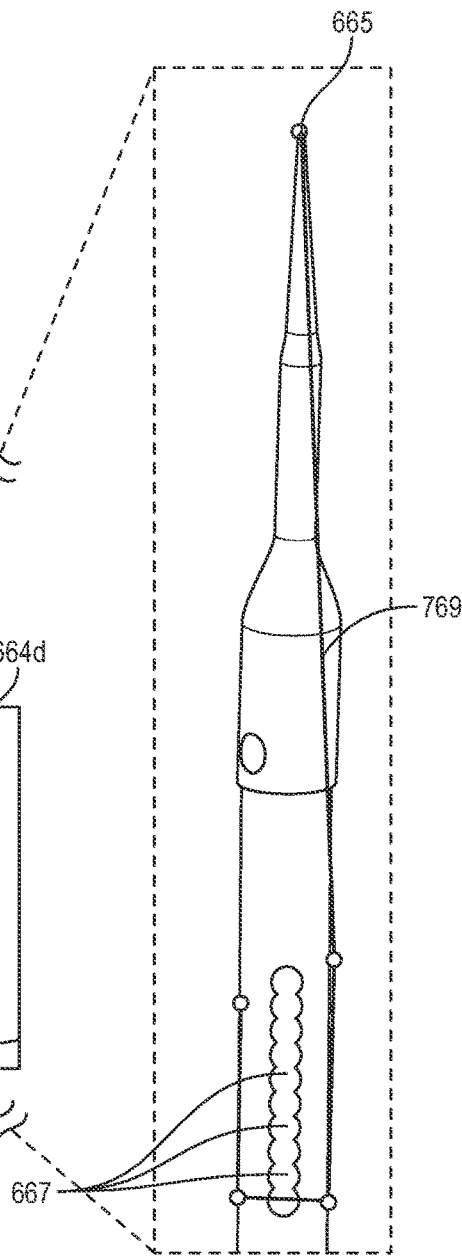
FIG. 7E is an enlarged view of a portion of FIG. 7D illustrating an identified tip point, multiple identified shaft points, and a shaft outline of the instrument in accordance with embodiments of the present technology.

At block 557, the method 550 can include identifying common features of the instrument 130 in the captured images. As shown in FIG. 6, for example, the common features can include one or more tip points 665 corresponding to the tip 132 of the instrument 130 and/or one or more shaft points 667 corresponding to the shaft 133 of the instrument 130. Similarly, FIG. 7E is an enlarged view of the fourth image 664*d* illustrating an identified tip point 665, multiple identified shaft points 667, and a shaft outline 769. Accordingly, the common features can comprise points, lines, volumes, outlines, and the like. The common features can be identified manually in the images 664 by a user (e.g., via user input), or the system 100 (e.g., the calibration processing device 109) can automatically identify the common features in the images 664. In some embodiments, the calibration processing device 109 can automatically detect the common features against the background 666 using classical methods such as feature extraction and segmentation. In some embodiments, the calibration processing device 109 can use machine learning algorithms to identify the common features. Implementing such a machine learning algorithm can include (i) receiving 3D models (e.g., computer-aided design (CAD) models), (ii) labeling/classifying features in the 3D models such as shaft points, tip points, etc., and (iii) training the machine learning algorithm based on the 3D models and labels. The instrument 130 can be generally cylindrical as shown in FIGS. 6-8, or can have any other shape.

At block 558, the method 550 can include generating a 3D representation/visualization of the instrument 130 based on the common features identified in the captured images. For example, the common features can be triangulated in 3D space (e.g., via back projection/reprojection) based on the known calibration and parameters of the cameras 112 relative to one another (e.g., as described in detail above with reference to block 551). In some embodiments, the 3D representation includes information specifying a relative position and/or orientation of the tip 132, the shaft 133, and/or another physical parameter of the instrument 130.

At block 559, the method 550 can include determining the instrument reference frame 453 of the instrument 130 based on the generated 3D representation of the instrument 130. For example, the calibration processing device 109 can define a reference frame having (i) a first axis (e.g., an X-axis) defined along the shaft 133 identified in the 3D representation, (ii) a second axis (e.g., a Y-axis) defined to be orthogonal to the first axis, and (iii) a third axis (e.g., a Z-axis) defined as the cross of the first and second axes. The second and third axes can be arbitrarily defined relative to the first axis when the instrument 130 is rotationally symmetric. When the instrument 130 is not symmetric, other features on the shaft 133 of the instrument 130, on the optical tracking structure 134, or elsewhere on the instrument 130 can be used to define the second and/or third axes relative to the first axis. For example, the system 100 can capture images of the optical tracking structure 134 (e.g., at block 556) and generate a 3D representation/visualization of the optical tracking structure 134 (e.g., at block 557). The 3D representation of the optical tracking structure 134 can be used to define the second axis relative to the first axis such that the axes are aligned in a known manner with the non-symmetric shape of the instrument 130. Accordingly, in some aspects of the present technology the system 100 can recover/determine the physical properties (e.g., shape, size) of the instrument 130 without previous knowledge of the instrument 130, such as a 3D model.

At block 560, the method 550 can include determining a third transform between the instrument reference frame 453 of the instrument 130 and the camera reference frame 450 of the cameras 112. FIG. 4 illustrates such an instrument-camera (CT) transform 457 between the instrument reference frame 453 and the camera reference frame 450. In some embodiments, the calibration processing device 109 determines the CT transform 457 in the same manner as it generates the 3D representation of the instrument. That is, for example, triangulation of the common features of the instrument 130 identified in the captured images of the instrument 130 can provide the transform (e.g., mapping) between the instrument reference frame 453 and the camera reference frame 450.

At block 561, the method 550 can include generating a fourth transform (e.g., the OTS-I transform 456) between the optical tracking structure reference frame 452 and the instrument reference frame 453. For example, the OTS-I transform 456 can be calculated as the product of the I-C transform 457, the C-T transform 454, and the T-OTS transform 455:

$$\text{Transform}_{OTS\text{-}I;456} = (\text{Transform}_{I\text{-}C;457})(\text{Transform}_{C\text{-}T;454})(\text{Transform}_{T\text{-}OTS;455})$$

That is, computing the I-C transform 457 can be used to recover/determine the rigid spatial relationship between the optical tracking structure 134 and the instrument 130 without previous/direct knowledge of the spatial relationship.

After block 560, each of the parameters 450-456 is known, and the system 100 can therefore determine the position and orientation of the instrument 130 within the scene 108 by tracking the markers 136. The system 100 can therefore present a visual representation of the instrument 130 in one or more output images of the scene 108 generated from images captured by the cameras 112. Accordingly, in some aspects of the present technology the system 100 can calibrate the instrument 130 for tracking (e.g., via the trackers 113 imaging the optical tracking structure 134) without previous knowledge of the physical properties of the instrument and/or the spatial relationship between the optical tracking structure 134 and the instrument 130.

In addition to calibrating instruments with unknown physical parameters and/or unknown attachments of optical tracking structures, the method 550 can be used to verify a calibration of an instrument with known physical parameters and a known spatial relationship between the instrument and an attached optical tracking structure. For example, the calibration can be initially carried out based on the known physical parameters of the instrument (e.g., a 3D model of the instrument) and the known (e.g., prespecified) OTS-I transform 456, as described in detail above. Then, the method 550 can be carried out to generate the 3D representation of the instrument (block 558) and compute the OTS-I transform 456 (block 561). The generated 3D representation can be compared to the known physical parameters and/or the determined OTS-I transform 456 can be compared to the known transform. If a difference of either comparison is outside a threshold tolerance, the system 100 can indicate that the calibration is potentially erroneous and/or rely on the parameters generated via the method 550 which reflect the current instrument positioned within the scene 108.

III. ADDITIONAL EXAMPLES

The following examples are illustrative of several embodiments of the present technology:

1. A method for calibrating an instrument having an attached tracking structure within an imaging system, the method comprising:
   capturing images of the instrument with a plurality of cameras of the imaging system;
   identifying common features of the instrument in the captured images;
   generating a three-dimensional (3D) representation of the instrument based on the common features;
   determining a reference frame of the instrument based on the generated 3D representation of the instrument;
   determining a first transform between the reference frame of the instrument and a reference frame of the cameras; and determining a second transform between the reference frame of the instrument and a reference frame of the tracking structure based on the first transform.

2. The method of example 1 wherein the method further comprises:
determining a third transform between the reference frame of the cameras and a reference frame of a plurality of trackers of the imaging system, wherein the trackers are configured to track a position and an orientation of the tracking structure;
determining a fourth transform between the reference frame of the trackers and the reference frame of the tracking structure; and
determining the second transform based on the first transform, the third transform, and the fourth transform.

3. The method of example 2 wherein determining the second transform includes computing a product of the first transform, the third transform, and the fourth transform.

4. The method of any one of examples 1-3 wherein the tracking structure is an optical tracking structure.

5. The method of any one of examples 1-4 where the instrument is a surgical instrument.

6. The method of any one of examples 1-5 wherein capturing the images of the instrument includes capturing the images of the instrument against a chromakey background.

7. The method of any one of examples 1-5 wherein capturing the images of the instrument includes capturing the images of the instrument against a light-emitting source background.

8. The method of any one of examples 1-7 wherein identifying the common features of the instrument includes receiving a user input manually identifying the commons features of the instrument in the captured images.

9. The method of any one of examples 1-7 wherein identifying the common features of the instrument includes automatically identifying the commons features of the instrument in the captured images using a feature extraction and segmentation algorithm.

10. The method of any one of examples 1-9 wherein identifying the common features includes automatically identifying the commons features of the instrument in the captured images using a machine learning algorithm.

11. The method of any one of examples 1-10 wherein generating the 3D representation of the instrument includes triangulating the common features in 3D space.

12. An imaging system, comprising:
a plurality of cameras configured to capture images of an instrument having a tracking structure attached thereto;
a plurality of trackers configured to capture positional data of the tracking structure;
a processing device communicatively coupled to the cameras and the trackers; and
a non-transitory computer readable storage medium storing instructions that, when executed by the processing device, cause the processing device to—
identify common features of the instrument in the captured images;
generate a three-dimensional (3D) representation of the instrument based on the common features;
determine a reference frame of the instrument based on the generated 3D representation of the instrument;
determine a first transform between the reference frame of the instrument and a reference frame of the cameras; and
determine a second transform between the reference frame of the instrument and a reference frame of the tracking structure based on the first transform.

13. The imaging system of example 12 wherein the instructions, when executed by the processing device, further cause the processing device to—
determine a third transform between the reference frame of the cameras and a reference frame of the trackers;
determine a fourth transform between the reference frame of the trackers and the reference frame of the tracking structure; and
determine the second transform based on the first transform, the third transform, and the fourth transform.

14. The imaging system of example 13 wherein the instructions, when executed by the processing device, further cause the processing device to determine the second transform by computing a product of the first transform, the third transform, and the fourth transform.

15. The imaging system of any one of examples 12-14 wherein the cameras and the trackers are fixedly mounted to a common frame.

16. The imaging system of any one of examples 12-16 wherein the cameras and the trackers are fixed in position and orientation relative to one another.

17. A method of tracking an instrument through a scene, the method comprising:
capturing images of the instrument with a plurality of cameras of an imaging system;
identifying common features of the instrument in the captured images;
generating a three-dimensional (3D) representation of the instrument based on the common features;
determining a reference frame of the instrument based on the generated 3D representation of the instrument;
determining a first transform between the reference frame of the instrument and a reference frame of the cameras;
determining a second transform between the reference frame of the cameras and a reference frame of a plurality of trackers of the imaging system;
determining a third transform between the reference frame of the trackers and a reference frame of a tracking structure attached to the instrument;
determining a fourth transform between the reference frame of the instrument and the reference frame of the tracking structure based on the first transform, the second transform, and the third transform;
tracking a position and orientation of the tracking structure through the scene with the trackers; and
applying the fourth transform to the position and orientation of the tracking structure to track a position and orientation of the instrument.

18. The method of example 17 wherein the method further comprises:
capturing images of the scene with the cameras;
generating an output image of the scene based on the captured images of the scene; and
displaying a representation of the instrument within the output image based on the second transform, the third transform, and the fourth transform.

19. The method of example 17 or example 18 wherein the cameras and the trackers are fixed in position and orientation relative to one another.

20. The method of any one of examples 17-19 wherein identifying the common features includes automatically identifying the commons features of the instrument in the captured images using a machine learning algorithm.

IV. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of tracking an instrument through a scene, the method comprising:
    capturing images of the instrument with a plurality of cameras of an imaging system;
    identifying common features of the instrument in the captured images;
    generating a three-dimensional (3D) representation of the instrument based on the common features;
    determining a reference frame of the instrument based on the generated 3D representation of the instrument;
    determining a first transform between the reference frame of the instrument and a reference frame of the cameras;
    determining a second transform between the reference frame of the cameras and a reference frame of a plurality of trackers of the imaging system;
    determining a third transform between the reference frame of the trackers and a reference frame of a tracking structure attached to the instrument;
    determining a fourth transform between the reference frame of the instrument and the reference frame of the tracking structure based on the first transform, the second transform, and the third transform;
    tracking a position and orientation of the tracking structure through the scene with the trackers; and
    applying the fourth transform to the position and orientation of the tracking structure to track a position and orientation of the instrument.

2. The method of claim 1 wherein the method further comprises:
    capturing images of the scene with the cameras;
    generating an output image of the scene based on the captured images of the scene; and
    displaying a representation of the instrument within the output image based on the second transform, the third transform, and the fourth transform.

3. The method of claim 1 wherein the cameras and the trackers are fixed in position and orientation relative to one another.

4. The method of claim 1 wherein identifying the common features includes automatically identifying the commons features of the instrument in the captured images using a machine learning algorithm.

5. The method of claim 1 wherein determining the fourth transform includes computing a product of the first transform, the second transform, and the fourth-third transform.

6. The method of claim 1 wherein the tracking structure is an optical tracking structure.

7. The method of claim 1 where the instrument is a surgical instrument.

8. The method of claim 1 wherein capturing the images of the instrument includes capturing the images of the instrument against a chromakey background.

9. The method of claim 1 wherein capturing the images of the instrument includes capturing the images of the instrument against a light-emitting source background.

10. The method of claim 1 wherein identifying the common features of the instrument includes receiving a user input manually identifying the commons features of the instrument in the captured images.

11. The method of claim 1 wherein identifying the common features of the instrument includes automatically identifying the commons features of the instrument in the captured images using a feature extraction and segmentation algorithm.

12. The method of claim 1 wherein identifying the common features includes automatically identifying the commons features of the instrument in the captured images using a machine learning algorithm.

13. The method of claim 1 wherein generating the 3D representation of the instrument includes triangulating the common features in 3D space.

14. An imaging system, comprising:
    a plurality of cameras configured to capture images of an instrument having a tracking structure attached thereto;
    a plurality of trackers configured to capture positional data of the tracking structure;
    a processing device communicatively coupled to the cameras and the trackers; and
    a non-transitory computer readable storage medium storing instructions that, when executed by the processing device, cause the processing device to identify common features of the instrument in the captured images;
    generate a three-dimensional (3D) representation of the instrument based on the common features;
    determine a reference frame of the instrument based on the generated 3D representation of the instrument;
    determine a first transform between the reference frame of the instrument and a reference frame of the cameras;

determine a second transform between the reference frame of the cameras and a reference frame of the trackers;
determine a third transform between the reference frame of the trackers and a reference frame of the tracking structure;
determine a fourth transform between the reference frame of the instrument and the reference frame of the tracking structure based on the first transform, the second transform, and the third transform;
track a position and orientation of the tracking structure through the scene with the trackers; and
apply the fourth transform to the position and orientation of the tracking structure to track a position and orientation of the instrument.

15. The imaging system of claim 14 wherein the instructions, when executed by the processing device, further cause the processing device to determine the fourth transform by computing a product of the first transform, the second transform, and the third transform.

16. The imaging system of claim 14 wherein the cameras and the trackers are fixedly mounted to a common frame.

17. The imaging system of claim 14 wherein the cameras and the trackers are fixed in position and orientation relative to one another.

18. The imaging system of claim 14 wherein the instructions, when executed by the processing device, further cause the processing device to identify the common features of the instrument by receiving a user input manually identifying the commons features of the instrument in the captured images.

19. The imaging system of claim 14 wherein the instructions, when executed by the processing device, further cause the processing device to identify the commons features of the instrument in the captured images using a feature extraction and segmentation algorithm.

20. The imaging system of claim 14 wherein the instructions, when executed by the processing device, further cause the processing device to identify the common features by automatically identifying the commons features of the instrument in the captured images using a machine learning algorithm.

\* \* \* \* \*